(12) United States Patent
Neer

(10) Patent No.: US 8,366,670 B2
(45) Date of Patent: Feb. 5, 2013

(54) POWERHEAD OF A POWER INJECTION SYSTEM

(75) Inventor: Charles S. Neer, Cincinnati, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 477 days.

(21) Appl. No.: 12/013,656

(22) Filed: Jan. 14, 2008

(65) Prior Publication Data

US 2008/0108941 A1   May 8, 2008

Related U.S. Application Data

(62) Division of application No. 11/073,883, filed on Mar. 7, 2005, which is a division of application No. 10/964,003, filed on Oct. 13, 2004, now Pat. No. 7,507,221.

(51) Int. Cl.
*A61M 1/00* (2006.01)
*A61M 31/00* (2006.01)
*A61B 6/00* (2006.01)

(52) U.S. Cl. .................. 604/151; 600/431; 604/507

(58) Field of Classification Search .............. 604/151, 604/131, 65; 600/431, 432
See application file for complete search history.

(56) References Cited

U.S. PATENT DOCUMENTS

| | | | |
|---|---|---|---|
| 4,044,757 A | 8/1977 | McWhorter et al. | |
| 4,585,435 A | 4/1986 | Vaillancourt | |
| 4,677,980 A | 7/1987 | Reilly et al. | |
| 4,695,271 A | 9/1987 | Goethel | |
| 4,833,384 A | 5/1989 | Munro et al. | |
| 4,835,519 A | 5/1989 | Suzaki et al. | |
| 4,854,324 A | 8/1989 | Hirschman et al. | |
| 4,943,279 A * | 7/1990 | Samiotes et al. | 604/151 |
| 5,279,569 A | 1/1994 | Neer et al. | |
| D351,398 S | 10/1994 | Meinzer | |
| 5,364,377 A | 11/1994 | O'Neil | |
| 5,378,231 A | 1/1995 | Johnson et al. | |
| 5,520,653 A | 5/1996 | Reilly et al. | |
| 5,573,515 A | 11/1996 | Wilson et al. | |
| 5,628,309 A | 5/1997 | Brown | |
| 5,636,548 A * | 6/1997 | Dunn et al. | 73/313 |

(Continued)

FOREIGN PATENT DOCUMENTS

| | | |
|---|---|---|
| EP | 0192786 A3 | 9/1986 |
| EP | 0454331 A1 | 10/1991 |

(Continued)

OTHER PUBLICATIONS

E-Z-EM, Inc., "E-Z-EM Injectors Empower Your CT Scanner", EMPOWERCT/EMPOWERCTA product brochure rev. Nov. 2003 (8 pages).

(Continued)

*Primary Examiner* — Kevin C Sirmons
*Assistant Examiner* — Andrew Gilbert

(57) ABSTRACT

A contrast media injection system detects the absolute position of the syringe ram using a non-contact sensor. A series of magnets and Hall-Effect sensors may be used or an opto-reflective system. Illuminated knobs that are connected to the drive mechanism for the syringe ram rotate with the drive and provide visual feedback on operation through the illumination. Analog Hall-Effect sensors are used to determine the presence or absence of magnets that identify the type of faceplate being used. The faceplates include control electronics, connected to the powerhead through connectors, which may be interchangeably used by the two faceplates. The faceplate electronics include detectors for automatically detecting the capacity of pre-filled syringes. Additional features include using historical data to provide optimum pressure limit values during an injection protocol, a removable memory device for storing and transferring information such as injection protocols and injector statistics, and password protection of such protocols.

10 Claims, 7 Drawing Sheets

U.S. PATENT DOCUMENTS

| | | | |
|---|---|---|---|
| 5,651,775 | A | 7/1997 | Walker et al. |
| 5,662,612 | A | 9/1997 | Niehoff |
| 5,728,074 | A | 3/1998 | Castellano et al. |
| 5,747,938 | A | 5/1998 | Beard |
| 5,782,814 | A | 7/1998 | Brown et al. |
| 5,800,397 | A | 9/1998 | Wilson et al. |
| 5,814,015 | A | 9/1998 | Gargano et al. |
| 5,830,194 | A | 11/1998 | Anwar et al. |
| 5,840,026 | A | 11/1998 | Uber et al. |
| 5,865,805 | A | 2/1999 | Ziemba |
| 5,868,710 | A | 2/1999 | Battiato et al. |
| 5,913,844 | A | 6/1999 | Ziemba et al. |
| 5,925,022 | A | 7/1999 | Battiato et al. |
| 5,928,197 | A * | 7/1999 | Niehoff .................. 604/155 |
| 5,993,420 | A | 11/1999 | Hyman et al. |
| 5,999,106 | A | 12/1999 | Buckler |
| 6,001,066 | A * | 12/1999 | Canfield et al. ........... 600/559 |
| D423,537 | S | 4/2000 | Lee |
| 6,080,136 | A | 6/2000 | Trull et al. |
| 6,179,569 | B1 | 1/2001 | Kojima et al. |
| 6,201,554 | B1 | 3/2001 | Lands |
| 6,233,475 | B1 | 5/2001 | Kim et al. |
| 6,254,572 | B1 | 7/2001 | Knipfer et al. |
| D446,578 | S | 8/2001 | Jansen et al. |
| D452,003 | S | 12/2001 | Niermann |
| D452,313 | S | 12/2001 | Niermann |
| 6,339,718 | B1 | 1/2002 | Zatezalo et al. |
| 6,368,307 | B1 | 4/2002 | Ziemba et al. |
| 6,411,306 | B1 | 6/2002 | Miller et al. |
| 6,423,035 | B1 | 7/2002 | Das et al. |
| 6,450,963 | B1 | 9/2002 | Ackerman |
| 6,471,648 | B1 | 10/2002 | Gamelsky et al. |
| 6,482,185 | B1 | 11/2002 | Hartmann |
| 6,533,757 | B1 | 3/2003 | Lampropoulos et al. |
| 6,572,585 | B2 | 6/2003 | Choi |
| 6,643,537 | B1 | 11/2003 | Zatezalo et al. |
| D484,900 | S | 1/2004 | Lee et al. |
| D485,356 | S | 1/2004 | Evans |
| 6,673,033 | B1 | 1/2004 | Sciulli et al. |
| 6,673,048 | B1 | 1/2004 | Duchon et al. |
| 6,676,634 | B1 | 1/2004 | Havrilla et al. |
| 6,689,091 | B2 | 2/2004 | Bui et al. |
| 6,743,205 | B2 | 6/2004 | Dedig et al. |
| 6,795,137 | B1 | 9/2004 | Whitted et al. |
| 7,094,216 | B2 | 8/2006 | Trombley, III et al. |
| 7,794,429 | B2 * | 9/2010 | Niehoff .................. 604/152 |
| 2002/0016569 | A1 | 2/2002 | Critchlow et al. |
| 2002/0151804 | A1 | 10/2002 | O'Mahony et al. |
| 2002/0151854 | A1 | 10/2002 | Duchon et al. |
| 2002/0169415 | A1 | 11/2002 | Staats et al. |
| 2002/0175062 | A1 | 11/2002 | Etter et al. |
| 2002/0183616 | A1 | 12/2002 | Toews et al. |
| 2003/0009133 | A1 | 1/2003 | Ramey |
| 2003/0028145 | A1 | 2/2003 | Duchon et al. |
| 2003/0216643 | A1 | 11/2003 | Zatezalo et al. |
| 2003/0216692 | A1 * | 11/2003 | Fago et al. .................. 604/150 |
| 2003/0217986 | A1 | 11/2003 | Sidler |
| 2004/0045704 | A1 | 3/2004 | Bowles |
| 2004/0064041 | A1 | 4/2004 | Lazzaro et al. |
| 2004/0122369 | A1 | 6/2004 | Schriver et al. |
| 2004/0135078 | A1 | 7/2004 | Mandro et al. |
| 2004/0152979 | A1 | 8/2004 | Sakakibara et al. |
| 2004/0249276 | A1 | 12/2004 | Nemoto et al. |
| 2004/0249344 | A1 | 12/2004 | Nemoto et al. |
| 2005/0096593 | A1 | 5/2005 | Pope et al. |
| 2005/0148868 | A1 | 7/2005 | Fago et al. |
| 2005/0234428 | A1 | 10/2005 | Spohn et al. |
| 2006/0079842 | A1 | 4/2006 | Small et al. |
| 2006/0079843 | A1 | 4/2006 | Brooks et al. |
| 2006/0167415 | A1 | 7/2006 | Nemoto |
| 2006/0184122 | A1 | 8/2006 | Nemoto |
| 2009/0157146 | A1 * | 6/2009 | Linder et al. .................. 607/60 |
| 2010/0127807 | A1 * | 5/2010 | Hammond .................. 335/255 |

FOREIGN PATENT DOCUMENTS

| | | |
|---|---|---|
| EP | 1217598 A2 | 6/2002 |
| EP | 1449550 A1 | 8/2004 |
| EP | 1465101 A2 | 10/2004 |
| EP | 1074221 A2 | 2/2007 |
| WO | 93/25816 A1 | 12/1993 |
| WO | 03-105930 A2 | 12/2003 |
| WO | 2005/079892 A2 | 9/2005 |

OTHER PUBLICATIONS

E-Z-EM, Inc., "Empowerct Industrial Design Excellence Award Winner", product webpage 1995-2005 (3 pages).

E-Z-EM, Inc., "EMPOWERCT/EMPOWERCTA IRiSCT CT Injector Reporting Information System", 2005 product PowerPoint slide presentation (11 pages).

E-Z-EM, Inc., "Injector Systems Marketing Bulletin", sales memorandum Nov. 22, 2004 (1 page).

Birnbaum, et al., "Extravasation Detection Accessory: Clinical Evaluation in 500 Patients", Radiology 1999 (2 pages).

Schoepf, "Clinical Applications of Saline Bolus Chasing Techniques with the E-Z-EM Double Syringe Injection System for Contrast-Enhanced Multidetector-Row CT Angiography: CT Coronary Angiography", Tech Note 2004 (2 pages).

Medrad Avanta Fluid Management Injection System webpage Mar. 4, 2005 (2 pages).

Medrad Avanta Fluid Management Injection System webpage Jun. 21, 2005 (2 pages).

MEDRAD "When it Comes to Reliability, We've Made Quite a Mark" product brochure 1999 (4 pages).

MEDRAD IV Infusion product brochure 2004 (2 pages).

MEDRAD "A Dedicated Dual Head CT Injection System" product flyer 2004 (1 page).

MEDRAD CT DualFlow product brochure 2004 (2 pages).

MEDRAD Stellant CT Injection Systems product brochure 2004 (4 pages).

Gridley, "Significant Reduction of Contrast Dose in Chest CT Angiography Utilizing a Dual Injector System with Saline Flush", clinical information 2003 (1 page).

Haage, et al., "Reduction of Contrast Material Dose and Artifacts by a Saline Flush Using a Double Power Injector in Helical CT of the Thorax", American Roentgen Ray Society, Apr. 2000, pp. 1049-1053.

TECHNOVATE Aquaject product flyer, 2004 (1 page).

European Patent Office, International Search Report issued in corresponding PCT Application serial No. PCT/US2005/036459 dated Sep. 27, 2006 (6 pages).

European Patent Office, International Search Report issued in corresponding PCT Application serial No. PCT/US2005/136566 dated May 2, 2006 (9 pages).

* cited by examiner

POWERHEAD OF A POWER INJECTION SYSTEM

CROSS REFERENCE TO RELATED APPLICATIONS

This application is a divisional of application Ser. No. 11/073,883, filed Mar. 7, 2005, which is a divisional of application Ser. No. 10/964,003, filed Oct. 13, 2004, now U.S. Pat. No. 7,507,221. This application is related to application Ser. No. 12/013,628, entitled POWERHEAD OF A POWER INJECTION SYSTEM, filed on Jan. 14, 2008, now U.S. Pat. No. 7,727,196, application Ser. No. 12/013,644 entitled POWERHEAD OF A POWER INJECTION SYSTEM filed Jan. 14, 2008, now U.S. Pat. No. 8,282,595, application Ser. No. 12/013,647, entitled POWERHEAD OF A POWER INJECTION SYSTEM, filed Jan. 14, 2008, now U.S. Pat. No. 8,180,434, application Ser. No. 11/551,804, filed Oct. 23, 2006, Application No. PCT/US05/36459, filed Oct. 12, 2005, now expired, Application No. PCT/US05/36566, filed Oct. 12, 2005, now expired, Application No. 29/227,127, filed Apr. 7, 2005, now Pat. No. D550,838, application Ser. No. 29/227,139, filed Apr. 7 2005, now Pat. No. D572,818, application Ser. No. 29/227,140, filed Apr. 7, 2005, now Pat. No. D547,447, application Ser. No. 11/073,915, filed Mar. 7, 2005, application Ser. No. 11/073,910, filed Mar. 7, 2005, application Ser. No. 11/073,902, filed Mar. 7, 2005, now U.S. Pat. No. 8,277,416, and application Ser. No. 10/964,002, filed Oct. 13, 2004, now abandoned. All of these applications are hereby incorporated by reference herein in their entirety.

FIELD OF THE INVENTION

The present invention relates to contrast media injector systems and, more particularly to improvements thereto.

BACKGROUND OF THE INVENTION

In many medical environments, a medical fluid is injected into a patient during diagnosis or treatment. One example is the injection of contrast media into a patient to improve CT, Angiographic, Magnetic Resonance or Ultrasound imaging, using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling mounted arm.

The injection head is typically mounted on the arm in a pivotal manner, so that the head may be tilted upward (with the syringe tip above the remainder of the syringe) to facilitate filling the syringe with fluid, and downward (with the syringe tip below the remainder of the syringe) for injection. Tilting the head in this manner facilitates removal of air from the syringe during filling, and reduces the likelihood that air will be injected into the subject during the injection process. Nevertheless, the potential for accidentally injecting air into a patient remains a serious safety concern.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

Thus, at least part of the injection process is typically automatically controlled; however, the filling procedure, and typically some part of the injection procedure, are normally performed by an operator, using hand-operated movement controls on the injector head. Typically, the hand-operated movement controls include buttons for reverse and forward movement of the injector drive ram, to respectively fill and empty the syringe. In some cases, a combination of buttons is used to initiate movement of the ram or to control ram movement speed. The injector head also typically includes a gauge or display for indicating injection parameters to the operator, such as the syringe volume remaining, for the operator's use when controlling the injector head. Unfortunately, operators have found it cumbersome to use the hand-operated movement buttons and to read the injector head gauges and displays, for several reasons, not the least of which is the necessary tilting of the injector head between the upward, filling position to the downward, injection position, changing the positions of the hand-operated movement buttons relative to the operator, and at some tilt angles rendering the gauges or displays difficult to read.

In many applications, it is desirable to use an injector with multiple different syringe sizes. For example, it may be desirable to use a smaller syringe for pediatric use than for adult use, or where a particular procedure requires a smaller volume of fluid. To facilitate the use of different syringe sizes, injectors have been constructed with removable faceplates, where each of the various faceplates is configured for a particular syringe size. Typically, the injector is able to adjust injection parameters by detecting which faceplate is mounted to the injector, for example using a magnetic detector mounted to the front surface of the injector housing to detect the presence or absence of a magnet in the faceplate. Unfortunately, the necessity of incorporating a magnetic detector into the outer housing of the injector head increases the complexity and expense of manufacturing the injector head.

Recently, one development in power injectors has been the introduction of dual headed injectors, that is, an injector with two drive systems and mountings for two syringes. The software for the injector provides for independent control of these drive systems using both manual controls and programmed injection routines in response to a stored sequence. Such dual headed injectors allow multiple fluids to be injected during a sequence without changing a syringe or other equipment.

Regardless of the benefits of current power injector systems, whether single head or dual head, improvements and advances in this field continue to be desirable goals and will ensure that such equipment becomes easier to use, increase in functionality, and become more reliable and efficient in operation.

SUMMARY OF THE INVENTION

Accordingly, embodiments of the present invention relate to improving power injectors that are used to inject contrast media and other fluids in a patient or animal.

One aspect of the present invention relates to determining an absolute position of a syringe ram, without requiring contact between the position sensor and the drive mechanism of the syringe ram. In particular, a series of Hall-Effect sensors are arranged along a path that the syringe ram travels, and a magnet is coupled to a portion of the syringe ram. In any position of the syringe ram, the sensors can detect the magnet and based on which sensors are detecting the magnet, the position of the syringe ram can be determined.

In a specific embodiment of this aspect, analog Hall-Effect sensors are utilized, enabling increased accuracy in determining the position of the magnet relative to the sensors.

A second aspect of the present invention is similar except that it uses an optical sensor. In accordance with this aspect, a fixed optical sensor transmits radiation to a reflective surface that is attached to a moving portion of the syringe ram. The strength of the reflected signal at the optical sensor is indicative of the distance from the sensor to the reflective surface. Accordingly, a position of the syringe ram can be determined based on the reflected signal.

Another aspect of the present invention relates to a manual control knob that is operatively coupled with the mechanism that moves the syringe ram. Because of this operative coupling, the knob rotates when the syringe ram is moving under programmed control. Also, the knob rotates at a speed that is directly indicative of the relative speed of the syringe ram. The knob is advantageously illuminated such that its rotation and speed of rotation is easily discernible. Accordingly, the control knob movement provides direct feedback about the operation of the syringe ram. In disclosed embodiments, this feedback is enhanced by changing the color of illumination of the knob to reflect the operative mode of the injector.

Yet another aspect of the present invention relates to using analog Hall-Effect sensors to determine what type of faceplate is attached to an injector powerhead. Instead of relying on fixed-threshold digital Hall-Effect sensors, the analog sensors are used to calibrate a threshold value for each different faceplate. The calibrated thresholds can, therefore, accommodate variations in manufacturing tolerances and magnet strength. For each sensor, a signal level is determined with the faceplate attached and the faceplate detached. The threshold value is set between those two signal levels. In disclosed embodiments, to permit a wider range of magnet combinations and thereby accommodate more faceplates, the Hall-effect sensors may be sensitive to polarity of the magnet, so that the North-South orientation of the magnets in the faceplate may be included in the properties detected by the Hall-effect sensor to identify a faceplate.

Still another aspect of the present invention relates to safely setting a pressure limit value for a protocol that prevents excessive pressures from occurring. In accordance with this aspect, historical data is acquired for a protocol when in it executed. The historical data can indicate the highest pressure encountered for this protocol or the average pressure encountered for this protocol. The injector system interface screen can then suggest a pressure limit value for the operator to input based on this historical data. Furthermore, statistical analysis of historical pressures for a protocol may be used to identify unusual or outlying conditions for the purpose of generating operator warning signals.

One additional aspect of the present invention relates to a detection circuit that determines the fill level of a syringe. An array of sensors is arranged along the longitudinal axis of the syringe, so that each transmits a signal and receives a reflected signal. Based on which sensor detects a reflected signal, the location of a plunger disc within the syringe may be located. Based on this location, the fill level of the syringe can be determined.

A further aspect of the present invention relates to an injector having a removable memory device for download and upload of injector information, such as injector configuration information and injector usage statistics. Injector configuration information stored on the memory device may include injection sequences or protocols that have been configured by an operator, allowing those protocols to be readily transferred from one injector to another, and/or preserved as the remainder of the injector is serviced. Injector usage statistics stored on the memory device may include hours of operation, number of injections, pressures and flow rates achieved and protocols utilized, as well as software updates for the injector. The memory socket may be included on the powerhead, or in other connected parts of the injector system, such as the console or powerpack. In a related aspect, stored protocols may be retrieved and modified by the injector prior to use, but a password may be required before permitting the overwriting of the stored protocol.

A further aspect of the present invention relates to an injector powerhead for injection from first and second syringes, having multiple syringe accessory connectors, and circuitry for identifying whether an accessory coupled to one of those connectors is associated with the first or second syringe, thus freeing the operator from the burden of connecting a syringe accessory to an appropriate one of the syringe connectors.

It will be appreciated that principles of the present invention are applicable to the injection of contrast media into a patient to improve CT, Angiographic, Magnetic Resonance or Ultrasound imaging, or any other application involving injection of fluids using a powered, automatic injector.

DETAILED DESCRIPTION OF THE INVENTION

Figure 1A:
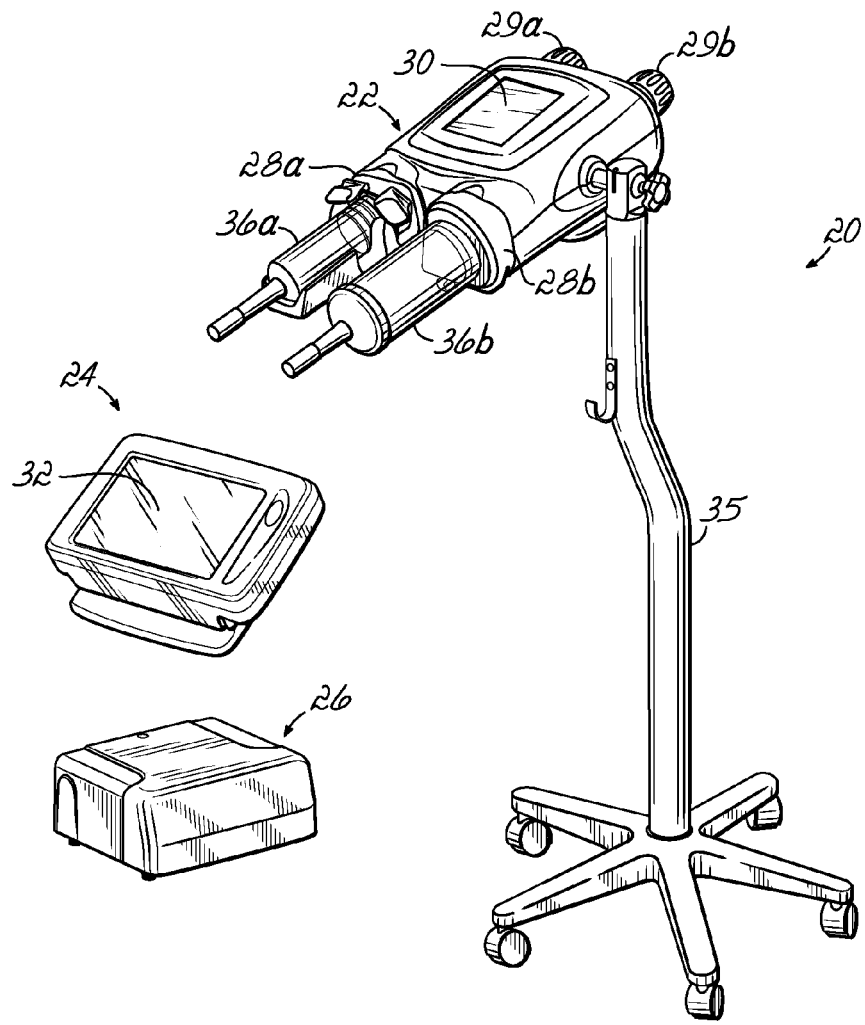
FIG. 1A illustrates a power injector system according to the principles of the present invention.

Referring to FIG. 1A, an injector 20 in accordance with the present invention includes various functional components, such as a powerhead 22, a console 24 and powerpack 26. Syringes 36a and 36b are mounted to the injector 20 in faceplates 28a and 28b of the powerhead 22, and the various injector controls are used to fill the syringe with, e.g., contrast media for a CT, Angiographic or other procedure, which media is then injected into a subject under investigation under operator or pre-programmed control.

The injector powerhead 22 includes a hand-operated knobs 29a and 29b for use in controlling the movement of the internal drive motors engaged to syringes 36a and 36b, and a display 30 for indicating to the operator the current status and operating parameters of the injector. The console 24 includes a touch screen display 32 which may be used by the operator to remotely control operation of the injector 20, and may also be used to specify and store programs for automatic injection by the injector 20, which can later be automatically executed by the injector upon initiation by the operator.

Powerhead 22 and console 24 connect through cabling (not shown) to the powerpack 26. Powerpack 26 includes a power supply for the injector, interface circuitry for communicating between the console 24 and powerhead 22, and further circuitry permitting connection of the injector 20 to remote units such as remote consoles, remote hand or foot control switches, or other original equipment manufacturer (OEM) remote control connections allowing, for example, the operation of injector 20 to be synchronized with the x-ray exposure of an imaging system.

Powerhead 22 is mounted to a wheeled stand 35, which includes a support arm for supporting powerhead 22 for easy positioning of powerhead 22 in the vicinity of the examination subject. Console 24 and powerpack 26 may be placed on a table or mounted on an electronics rack in an examination room. Other installations are also contemplated however; for example, powerhead 22 may be supported by a ceiling, floor or wall mounted support arm.

Figure 1B:
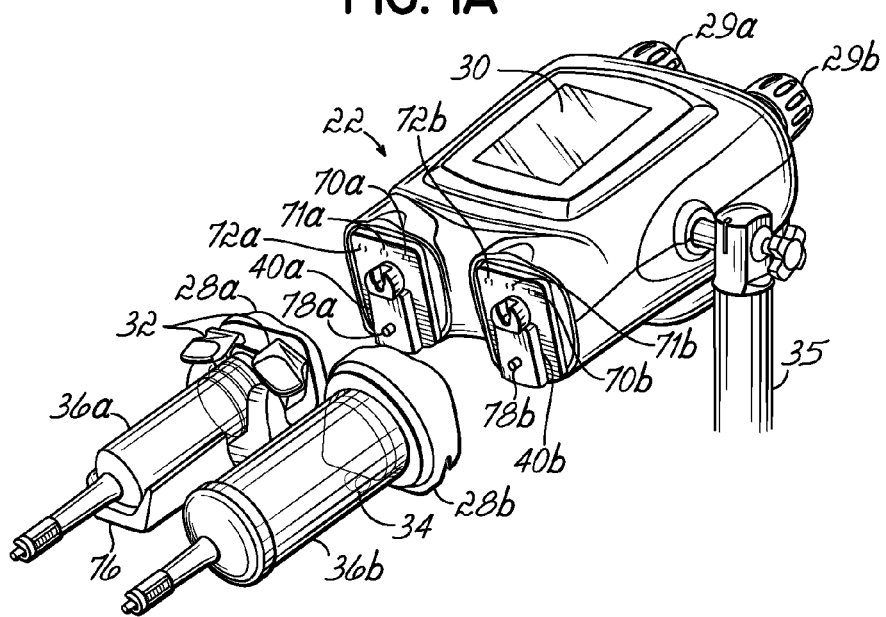
FIG. 1B illustrates the components of the powerhead of that system.

Referring to FIG. 1B, details of the powerhead 22 can be seen. In FIG. 1B, faceplates 28a and 28b have been removed, illustrating details of the mountings 40a and 40b for the faceplates. Two different faceplates are shown in FIG. 1B. Faceplate 28a is designed for mounting a 125 ml syringe, and uses mechanical structures similar to those disclosed in U.S. patent application Ser. No. 10/211,726, which is hereby incorporated by reference herein in its entirety. These structures include movable arms 32 which rotate into and out of engagement with the cylindrical body of the syringe to engage the syringe. The syringe is installed perpendicular to its axis to engage a button on the rearward face of the syringe with a jaw on the end of the drive ram, as shown in the above-referenced patent application. Faceplate 28b is designed for mounting a 200 ml front-loading syringe, and uses mechanical structures similar to those illustrated in U.S. Pat. No. 5,300,031, which is hereby incorporated by reference herein in its entirety. These structures include a rotating cam, rotatable via an externally-extending arm 34 to cause translation of the faceplate 28b relative to the mounting 40b. The rotating cam further includes engaging keys that mate to slots on a rearward end of syringe 36b so that rotation of the syringe is linked to rotation of the cam and translation of the faceplate. The translation of faceplate 28b relative to mounting 40b causes a button on a rearward face of the plunger in syringe 36b to translate into and out of engagement with a jaw on the end of the drive ram, as shown in U.S. Pat. No. 5,300,031.

The circuitry internal to powerhead 22 includes, in the area of mountings 40a and 40b, Hall effect sensors for detecting magnets in the corresponding faceplate. Specifically, there are Hall effect sensors on the circuit board internal to injector powerhead 22 at each of positions 70a/70b, 71a/71b and 72a/72b. These sensors detect the presence or absence of a magnet in the faceplate adjacent to positions 70a/70b, 70a/71b and 72a/72b. The sensors at positions 71a/71b and 72a/72b are used to identify the faceplate mounted to powerhead 22, that is, the presence or absence of a magnet in a faceplate corresponding to these locations identifies the faceplate type and thus the syringe size being used on that side of the injector. The sensors at positions 70a/70b have an alternative purpose of identifying whether the faceplate is closed or open. Mountings 40a and 40b include, at locations 70a and 70b, magnetic conductors for carrying magnetic flux to a sensor on an internal circuit board, as discussed further below with reference to FIG. 7. The faceplates 28a and 28b each include a magnet in the movable mounting structures, that is, faceplate 28a includes a magnet within one of the movable arms 32, and faceplate 28b includes a magnet within the internal rotating cam coupled to arm 34. This magnet is positioned so that when the syringe and faceplate are engaged for injection, the magnet aligns with the magnetic conductor at location 70a/70b, triggering the sensor internal to powerhead 22. Because the movable structures in the faceplates are not as close to mountings 40a and 40b as magnets at locations 71a/71b and 72a/72b, and for this reason a magnetic conductor is included at locations 70a/70b to ensure flux is channeled to the sensors internal to powerhead 22.

Mountings 40a and 40b further include a magnetic conductor 78a and 78b, useable to identify whether a faceplate has been connected to the A or B side of the injector powerhead, as elaborated below. The magnetic conductors 78a and 78b carry flux from magnets internal to the faceplate. These magnets have opposite polarities and/or only one conductor 78a/78b contains a magnet, so that the positioning of a faceplate on the A or B side of the injector may be distinguished by a sensor in faceplates with appropriate sensing electronics, such as the 125 ml faceplate 28a discussed below.

Faceplate 28a notably includes a cradle housing 76 within which the syringe 36a is installed. Cradle housing 76 provides mechanical support for syringe 36a and may further house sensors such as are discussed in detail below with reference to FIGS. 10 and 11A through 11C.

Although the powerhead 22 discussed herein is a dual head injector, embodiments of the present invention explicitly contemplated single head injectors as well.

Figure 2:
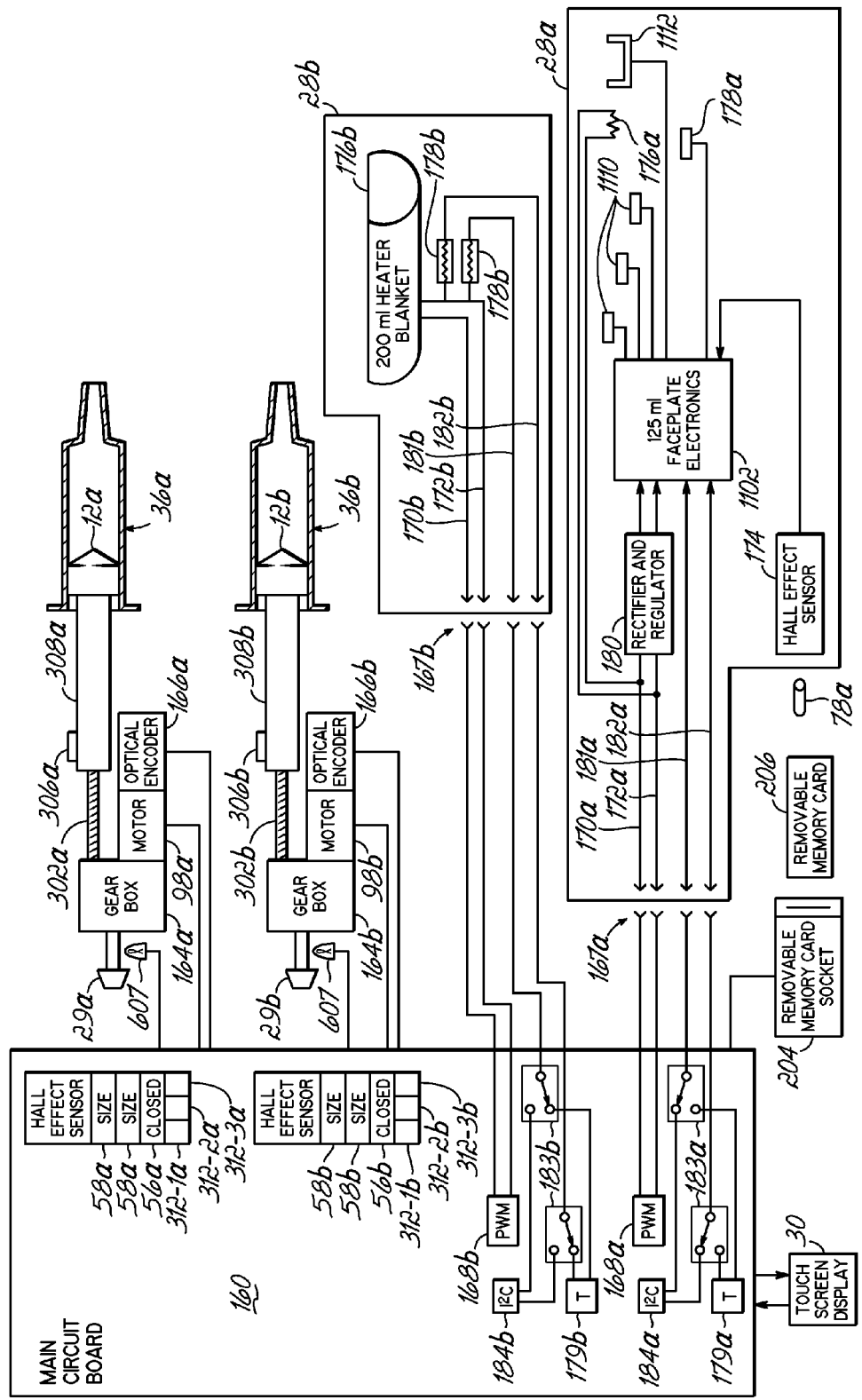
FIG. 2 illustrates an electrical block diagram view of major subcomponents of a powerhead of FIG. 1B.

Referring to FIG. 2, the powerhead includes a circuit board 160 including a microprocessor to perform communications with the powerpack 26 (FIG. 1). A suitable microprocessor is the Motorola/Freescale MCF5282, which is a "Coldfire" family microprocessor suitable for embedded applications. The circuit board generates displays on display 30, receives and forwards touch information from the interface display 30, controls the motor drives and receives feedback information regarding those motor drives, and controls illumination of the manual knobs 29a and 29b mounted on the rear of the powerhead.

The motors 98a and 98b are coupled to gear boxes 164a and 164b which translate rotary motion of the motor to linear translation of the plunger. One suitable motor is a Brushless DC Motor part number N2341 manufactured by Pittman of 343 Godshall Drive, Harleysville, Pa. The rotation of each motor is detected by optical encoders 166a and 166b (encoders 166a and 166b essentially comprise a pinwheel which rotates between a light source and a light detector to produce electrical pulses). Encoders 166a and 166b send electrical pulses to circuit board 160, which relays them to powerpack 26, allowing CPU 52 on the powerpack to monitor movement of the motor. The motors 98a/98b further provide three phase signals indicative of the phases of excitation of the stator, which are also received and monitored by circuit board 160 to verify the operation of the motor and provide verification of motor rotation as detected by the encoder 166a and 166b.

FIG. 2 illustrates the control electronics utilized in faceplates coupled to the injector powerhead 22. Specifically, each faceplate includes various electrical elements, connectable to circuit board 160 via a four wire connector jack 167a/167b including four lines 170a/170b, 172a/172b, 181a/181b and 182a/182b.

As presently contemplated, each of the various types of faceplates includes a heater blanket or heating element. In a relatively simple faceplate such as the faceplate for 200 ml syringes as is shown at 28b in FIG. 1B, the faceplate electronics comprise the heater blanket 176b (which may be a film resistive element or other electrical heating device connected between lines 170b and 172b), and temperature sensors such as thermistors 178b thermally coupled thereto and connected to lines 181b and 182b for detecting the syringe temperature. In a relatively complex faceplate such as the faceplate for a 125 ml syringes as is shown at 28a in FIG. 1B, the faceplate electronics comprise heater elements 176a (which may be high temperature resistors mounted on a circuit board 1102 internal to faceplate 28a), a temperature sensor integrated circuit 179a, and also additional sensor electronics, as elaborated below.

Circuit board 160 includes pulse width modulation generating circuits 168a/168b which generate a pulse-width modulated signals on lines 170a/170b relative to ground on lines 172a/172b, to heat the faceplate heating element 176a/176b to a controlled temperature. The temperature of the heater 176a/176b is detected by a temperature sensing circuit to provide controlled feedback of the pulse width modulation from circuit 168a/168b.

In a 200 ml faceplate, as presently contemplated, temperature sensing is provided by a temperature sensing circuit 179a/179b, which is coupled to lines 181b and 182b, and measures the current through or voltage drop across thermistors 178b in the 200 ml faceplate, relative to ground on line 172b, to detect the temperature of the syringe. The sensed temperature is converted to a digital value within circuit 179a/179b in circuit board 160, and the result is used to control the pulse width modulated signal on line 170b.

In a 125 ml faceplate, as presently contemplated, temperature sensing is provided by temperature sensing electronics 178a included on a circuit board 1102 and thermally coupled to the syringe in the faceplate. Detected temperature information is conveyed from circuit board 1102 to main circuit board 160 using a two-wire 12C interface over lines 181a and 182a. Within circuit board 160, the I$^2$C signal is coupled to an I$^2$C interface circuit 184 which receives digital communications of temperature readings, and delivers these to the microprocessor on circuit board 160 to control the pulse width modulated output of the connected circuit 168.

Circuit board 1102 draws power from a power rectification circuit 180 that is coupled to the pulse width modulated signal on lines 170a/172a that also drive resistive heater(s) 176a. Using this power, circuit board 1102 detects temperature as noted above, and further uses sensors 1110 and 1112, the function of which is elaborated below, to detect the plunger position of the syringe and syringe fill condition, and provide that information to the microprocessor on main circuit board 160 via the I$^2$C interface.

It will be noted that the circuitry on main circuit board 160 is adapted to permit either a 125 ml or a 200 ml faceplate, or potentially other types of faceplates with other control electronics, to be selectably connected to either or both of the interface jacks 167a/167b. Notably, switches 183a/183b are interposed between lines 181a/181b and 182a/182b and the I$^2$C interfaces 184a/184b and temperature circuits 179a/179b, thus permitting the selection by circuit board 160 of the appropriate connections for lines 181a/181b and 182a/182b based upon the type of faceplate connected to jack 167a and jack 167b.

The methodology used by the microprocessor in circuit board 160 to detect and control the type of faceplate connected to jack 167a, involves regularly setting a switches 183a to connect lines 181a and 182a to the corresponding I$^2$C interface 184a to determine if an I$^2$C connection can be made. If so, then operation proceeds using lines 181a and 182a as an I$^2$C connection, as with a 125 ml faceplate. If no connection can be made, then operation proceeds by connecting lines 181a and 182a via switches 183a to the corresponding temperature circuit 179a, to determine if there is a return current through those lines indicative of thermistors coupled to those lines. If so, then operation proceeds using lines 181a and 182a for temperature sensing as with a 200 ml faceplate. If no return current is detected, then it can be determined that no connection has been made to a faceplate on the A side of the injector, and an appropriate error signal generated. A similar methodology is used with lines 181b and 182b, switches 183b, I$^2$C interface 184b and temperature circuit 179b to determine and control the type of faceplate connected to jack 167b.

The control circuit 160 and faceplates are further adapted so that the operator may connect the faceplate on either the A or B side to either of connector jacks 167a and 167b without hindering operation of the injector. Specifically, as noted above, the injector 22 mounting areas 40a and 40b include magnetic indicators 78a and 78b which produce distinguishable magnetic signatures on the A and B side of the injector, such as the via the presence of a magnet in one side and the absence of a magnet on the other, or magnets of opposite North-South orientations on the respective A and B sides. A Hall effect sensor 174 on circuit board in the 125 ml faceplate 28a detects the magnetic flux from the magnetic indicator 78a when the faceplate is mounted on the injector, and delivers a signal to the faceplate electronics 1102. This signal is used to determine the I$^2$C address at which those electronics 1102 will communicate over lines 181a and 182a. As a consequence, when the I$^2$C interface circuits 184a/184b attempt to establish an I$^2$C connection over lines 181a/181b and 182a/182b, the address at which the connection is established determines whether the faceplate is on the A or B side of the injector, thus informing the microprocessor in circuit board 160 where the faceplate is located, so that the microprocessor may thereafter proceed appropriately in controlling injection on the identified side of the injector. This permits the microprocessor to control the injector powerhead 22 appropriately when two faceplates of the same type (e.g., 125 ml type) are placed on the A and B sides of the injector, and relieves the technician using the injector of any requirement to ensure that a faceplate's connection cord is connected to a particular one of the connector jacks 167a and 167b.

In one embodiment, circuit board 160 may include or be connected to a removable memory card socket 204 for connection to a removable memory card 206. Various available memory card technologies may be used for socket 204 and card 206, such as Memory Stick™ or Secure Digital Multimedia Memory Card (SD/MMC), as is conventionally used on digital cameras and portable computers and personal digital assistants. The removable memory device may be used to download and upload of various injector information, such as injector configuration information and injector usage statistics.

Injector configuration information stored on the memory device may include injection sequences or protocols that have been configured by an operator, allowing those protocols to be readily transferred from one injector to another. Typically the programming of an injection protocol involves the configuration of multiple steps each involving a flow rate and time or volume, as well as potentially various inject or scan delay times, pressure limits, a protocol name, and other parameters. A difficulty with injectors known in the prior art is that such data cannot be readily migrated from one injector to another, without reprogramming the second injector manually. When an injector is replaced as part of service, the stored protocols are lost, which is potentially a substantial source of frustration. Furthermore, in a hospital environment having multiple injectors, technicians wishing to use a protocol across multiple injectors would like to do so without reprogramming each of the injectors manually. A removable memory permitting upload and download of such protocol information can be used in either situation, thus dramatically simplifying the process of migrating protocols from one injector to another.

A further difficult with known injectors providing for stored protocols is that those protocols are difficult to manage effectively, because they are subject to change by technicians. For example, in the hospital environment noted above, technicians wishing to use a protocol repeatedly on an injector or multiple injectors may be required not only to create the protocol(s) but to monitor the stored protocol(s) to ensure it/they have not been changed by other technicians. This problem is particularly acute where one technician uses the protocol created by another as a "starting point" for an injection having slightly different parameters. In such a situation, there is a temptation for the second technician to modify the previously stored protocol entered by the first technician, and save those changes, overwriting the previously stored protocol.

It has been proposed, e.g., in U.S. Patent Publication 2004/0064041, page 31, to provide a "protocol lock", which may be based upon a password, to prevent editing of a protocol. As described in that publication, the protocol lock must be deactivated prior to implementing any changes to a protocol. This solution avoids the scenario described above. However, an outright lock of any editing of a protocol, has the disadvantage of preventing technicians from using a protocol created by another as a "starting point", even for one ad hoc use of the injector.

According to principles of the present invention, protocol storage is managed in an improved manner, as follows. A stored protocol may be associated with a password to prevent unauthorized modification of that stored protocol; however, the association of the password will only block storage of changes, and not use or modification in general. Without entering the password, it will still be possible to retrieve and modify of the parameters of the protocol for the purpose of an ad hoc injection; changes cannot, however, be saved overwriting the stored protocol without providing a password. In the absence of the password, however, the injector may provide a facility to store the changed protocol with a new name, if there is memory space available.

Furthermore, injector statistics may be uploaded from or downloaded to a removable memory as well, for example, as the remainder of the injector is serviced. Injector usage statistics that can be stored in the injector and moved to the memory device may include hours of operation, number of injections, pressures and flow rates achieved and protocols utilized. The collection of such statistics from an injector facilitates service and also aids in evaluation of injection needs for future marketing, and thus the ability to move these statistics to a removable memory will advance these objectives.

Circuit board 160 also detects the output of the Hall effect sensors mounted on the circuit board adjacent the faceplate mounting, which are identified at 56a/56b and 58a/58b on FIG. 2. Further details regarding the use of the sensors are provided below with reference to FIGS. 7-8.

In addition to the optical encoders 166a and 166b monitoring the position of the syringe ram as it moves, it is also useful to know the absolute position of the ram such as when the powerhead is powered on and off, for example. Previous approaches used linear potentiometers to monitor the position of the syringe ram. Then, as the injector was operated, the potentiometer moved as the ram moved. For example, a linear-movement potentiometer would move along with a portion of the ram; whereas a rotating potentiometer would rotate with the ball screw. With either type of potentiometer, a physical linkage between the ram and the potentiometer was needed.

Figure 3:
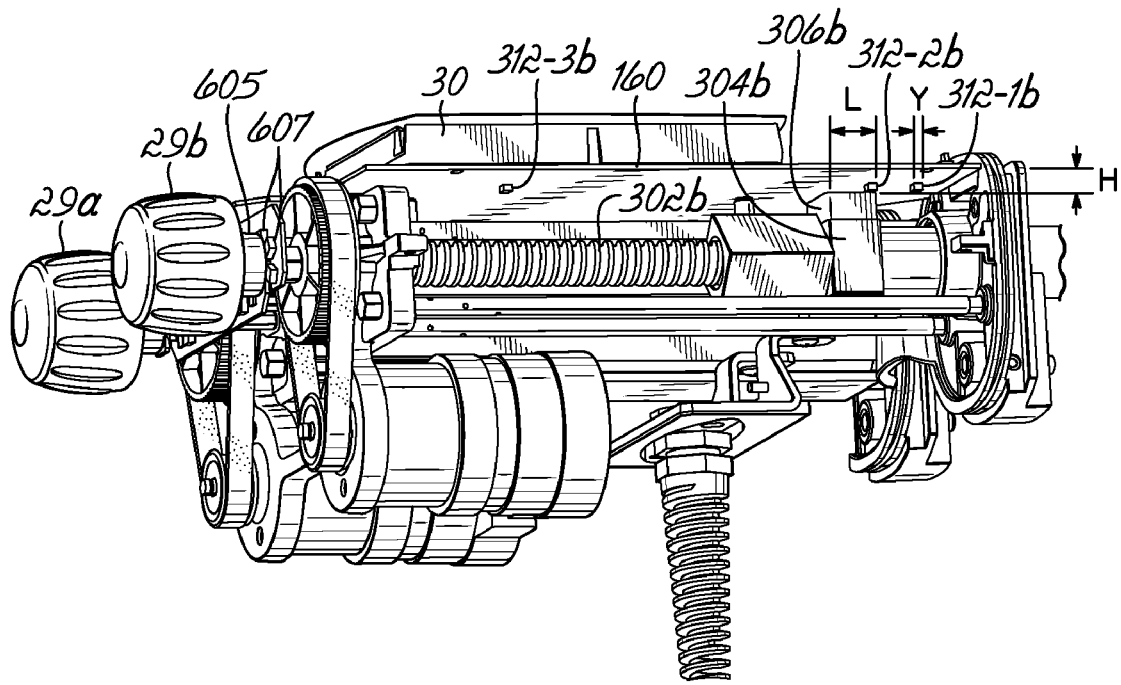
FIG. 3 is a partially disassembled view of the injector powerhead of FIG. 1B showing a syringe ram position detector in accordance with the principles of the present invention.

FIGS. 2 and 3 illustrate an alternative and improved approach that does not require contact with the ram in order to detect the absolute position of the syringe ram 308 and, also, detects this position upon powering up without the need to return to a "home" position.

The mechanism includes a two-pole magnet 306a/306b on each ram, a series of analog (or linear) Hall effect sensors 312-1a/312-1b, 312-2a/312-2b, 312-3a/312-3b for each faceplate, and control electronics on a circuit board 160. The magnet 306a/306b on each ram is advantageously as small as feasible with its poles on the longest axis. In operation, the magnet 306a/306b is placed on the ball screw nut and the ram attachment area. Hall-Effect sensors 312-1a/312-1b, 312-2a/312-2b, 312-3a/312-3b are placed nearby on circuit board 160 along the path the nut 304a/304b travels, as best seen in FIG. 3 (showing nut 304b, magnet 306b and sensors 312-1b, 312-2b and 312-3b). The clearance distance between each magnet 306 and the sensors 312 is made relatively small to ensure good magnetic detection, e.g., about 0.125 inches. The number of Hall effect sensors to use is dependent on the total distance the ram 308a/308b moves, the length, L, of the magnet 306a/306b, and the desired number of locations at which absolute position sensing is desired. While the present implementation utilizes three sensors 312-1a/312-1b, 312-2a/312-2b, 312-3a/312-3b for each ram, embodiments of the present invention contemplate using as few as one sensor and more sensors than three as well.

Control electronics such as a microcontroller or microprocessor communicate with the sensors 312-1a/312-1b, 312-2a/312-2b, 312-3a/312-3b in order to provide analysis of the signals from the sensors. Such control circuitry would preferably include non-volatile, and volatile, memory, analog-to-digital converters (ADCs), and various input and output circuitry as would be found on the main circuit board 160 (FIG. 2).

Figure 4:
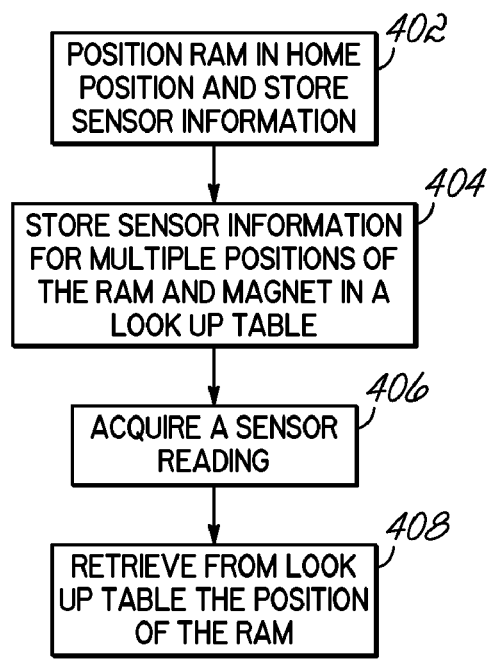
FIG. 4 depicts a flowchart of an exemplary algorithm for the operation of the detector of FIG. 3.

FIG. 4 depicts a flowchart of one exemplary algorithm for utilizing the encoder 166 of FIG. 2 in conjunction with magnetic positioning sensors. In accordance with this method, in step 402, the "home" position of the ram 308 is stored in microprocessor's memory along with the signals received from the Hall-Effect sensors 312-1a/312-1b, 312-2a/312-2b, 312-3a/312-3b in that position. Preferably, the analog signals from the Hall effect sensors are converted using an analog to digital converter (ADC) into appropriate signals for the microprocessor. Calibration of the sensors is continued in step 404 by storing a number of different entries that associate a particular set of sensor readings with a known position of the ram, including an end position. During operation of the injector during a sequence, the microprocessor may receive an indication of the Hall-Effect sensors, in step 406, and use a look-up operation, in step 408, to determine the absolute position of the syringe ram. This operation may involve performing interpolation between two known sensor states and their corresponding ram positions, to approximate the ram position from the sensor signals being received. Thus, the information stored in the microprocessor's memory permits identifying the stroke limit positions of the syringe ram and basic position information even if the ram is not returned to the "home" position after power is restored.

It will be noted that in the embodiment illustrated in FIG. 3, sensors 312-2b and 312-3b are spaced widely apart, limiting the collection of absolute position information when the ram magnet 306b is between these sensors. This has not been found to be a source of difficulty as typical injector usage has been found to involve bringing the ram to one end of the stroke or another on a fairly regular basis, at which times an absolute position may be determined with minimal interpolation error. Between such events the incremental position tracking using encoders 166a/166b and motor phase signals from motors 98a/98b has been found to be sufficiently accurate.

In an advantageous alternative embodiment, these potential limitations of the embodiment of FIG. 3 can be removed, and the sensors arranged such that the magnet 306 is always within sensing distance of two sensors (which necessarily limits the distance between sensors). Because the center of the magnet 306 has the same detectable flux density of no magnet, if only one sensor were used to detect the magnet and the magnet stopped centered over that sensor, then no absolute position could be determined. Thus, in one particular arrangement, the magnet 306 is sensed by at least two sensors as the center of the magnet passes over one of the sensors. There is preferably some overlap in the detection regions of the sensors as well to ensure that the magnet is reliably and accurately sensed. In such an embodiment, the magnet 304 has a length L and each sensor has an overlap length Y. The distance between two adjacent sensors, then, is selected to be L−Y. With this spacing criteria established, the total stroke length, D, of the injector can be used to determine the number of sensors, n. In particular, $D=n*(L-Y)$. The vertical distance, H, between the magnet 306 and the hall sensors 312-1a/312-1b, 312-2a/312-2b, 312-3a/312-3b is dependent on the strength of the magnet 306 as well as the sensitivity of the sensors 312. Using readily available magnets and sensors, this height would typically be around 0.125 inches; however, other distances are contemplated by the present invention as well.

Figure 5:
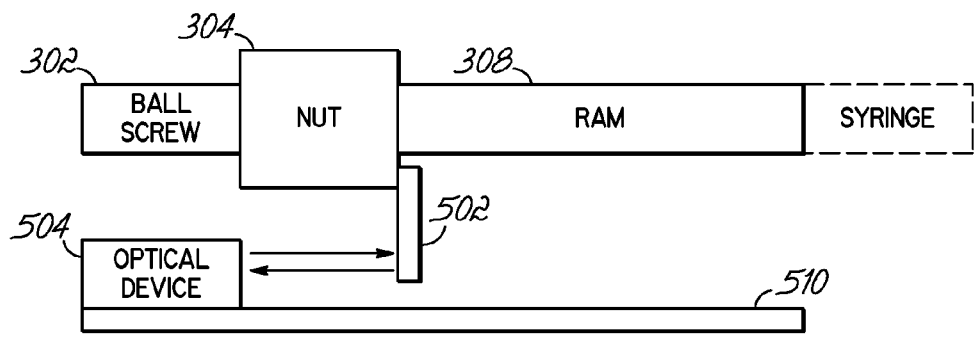
FIG. 5 schematically illustrates an alternative embodiment of a syringe ram position detector.

FIG. 5 depicts an alternative apparatus for determining the absolute position of a syringe ram 308 without requiring contact potentiometers as utilized in previous position monitoring circuits. A reflective surface 502 is attached to the nut 304 of the ram 308 such that a radiation source 504 may transmit radiation to the surface 502 and detect reflection therefrom. While the transmitter/detector device 504 of the figure is labeled as "optical", radiation energy outside of the visible spectrum is explicitly contemplated within the scope of the present invention. One exemplary optical distance measuring device 504, that may be mounted on a circuit board 510, is manufactured by Sharp Electronics as part number GP2D120. This particular optical device emits infrared radiation from an LED and senses the amount of light returned after it bounces off the reflector. The amount of light returned is proportional to the distance between the device and the reflector. Thus, within the device 504, the returned light is converted into an analog voltage that indicates the distance of the reflective surface. An ADC, such as that found on the main circuit board 160 (FIG. 2) can be used to convert this analog voltage into a digital signal used by a microprocessor to calculate the absolute position of the syringe ram 308. Similar to the method used in the algorithm of FIG. 4, a look up table could be used to store an associated pairs of voltage levels and encoded positions. As a result, the absolute position of the ram 308 may be determined by searching through the look-up table using a detect voltage level from the device 504.

Conventional power injectors would preferably use an optical device 504 that can detect distances from a range of approximately 1 cm to 30 cm. However, one of ordinary skill would recognize that a device other that the one identified above, or a specially designed discrete circuit, may be utilized to customize the range of distances that could be detected.

Automatic or power injectors as described herein automatically move a ram syringe so that contrast media or other fluids may fill a syringe or be expelled from a syringe. While such operation simplifies a number of tasks for operators, there are some instances in which an operator may want to manually control the movement of the syringe ram. Some injector consoles and powerheads provide push-buttons or similar mechanisms to move the syringe ram in one direction or the other, while other consoles and powerheads additionally provide a knob that a operator may rotate to effect movement of the syringe ram. A control bar/lever has also been used.

Operators running power injector equipment often exit the scanner room to avoid exposure to X-rays and other potentially harmful conditions within the scanner room. In such instances, the operator typically monitors the patient and the injector from a remotely located control room. As the injector carries out an injection protocol, the LEDs or display on the injector will changed according to the steps of the protocol and, also, the console typically includes a visual display that is updated as the protocol progresses. The indicators on the injector, however, are not directly connected with the operating mechanism of the injector, and furthermore, are not readily visible from a distance. This is a limitation of known injectors that is addressed by the injector described herein.

Figure 6:
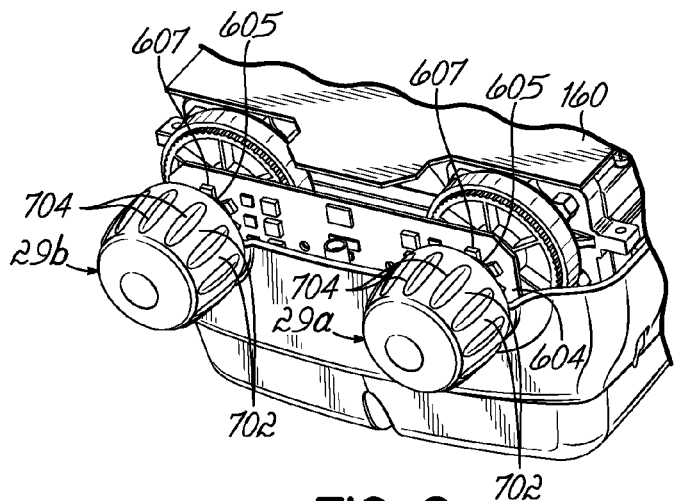
FIG. 6 is a partially disassembled view of the injector powerhead of FIG. 1B showing illuminated control knobs in accordance with the principles of the present invention.

FIG. 6 depicts the internal structures of the dual head injector powerhead 22 of the preceding figures, and the two separate manual control knobs 29a and 29b. According to the principles of the present invention, the manual actuation knobs 29a and 29b of the injector powerhead 22 are utilized to provide visual feedback to an operator that directly indicates the operating characteristics of the syringe ram. The manual knob is directly coupled to the drive screw, sometimes through gears, and is usually used to manually purge air from the system. In the case of a multiple-headed injector, each drive system has its own separate manual knob 29a and 29b that can be used to precisely expel fluid into, or withdraw fluid from, a patient. Because the knob 29a and 29b is connected to the ram and rotates at the same time the ram is injecting fluid into a patient, the rotation of the knob 29a and 29b during automatic injections provides direct feedback to the operator about the operation of the ram. For example, the rotation of the knob indicates movement of the ram as well as its relative speed. In one exemplary embodiment, the knobs 29a and 29b are illuminated so that their rotation can be observed easily from a distance and in low light conditions.

One or more LEDs 607 are used as a light source for lighting the inside of a knob. These LED's are electrically coupled to the circuit board 160 as shown in FIG. 2, but reside on a separate circuit board 604 adjacent to the knobs 29a and 29b. As illustrated in detail in FIG. 6, the knobs 29a and 29b include opaque regions 702 and transparent or translucent regions 704 spaced around their periphery. The opaque regions preferably are made of a relatively high-friction, soft feel material to provide an appealing and functionally effective tactile surface. One suitable material is commercially available under the name Santoprene. The longitudinal striping of the opaque and transparent or translucent regions causes light to be emitted from some portions of the knob but not from other portions. As the syringe ram moves, the operator may directly observe the rotation of the knob along with its relative speed from a remote location. In one exemplary embodiment, the internal structure of the knob preferably behaves as a light pipe 605 that guides the light emitted from the LEDs 607 to each of the transparent regions 704 of the knobs 29*a* and 29*b*.

Certain conventions have developed with power injectors that associate certain colors with the status of the injector. For example, in the past, LEDs of a particular color were illuminated to indicate whether the injector was enabled, not enabled, injecting, paused, pressure-limiting, etc. The LEDs 607 depicted in FIG. 6 may be used to maintain these conventions as well. Multi-color LEDs, therefore, may be used so that the knob 29*a*/29*b* is not simply illuminated but is illuminated in a color corresponding to the status of the injector.

Figure 7:
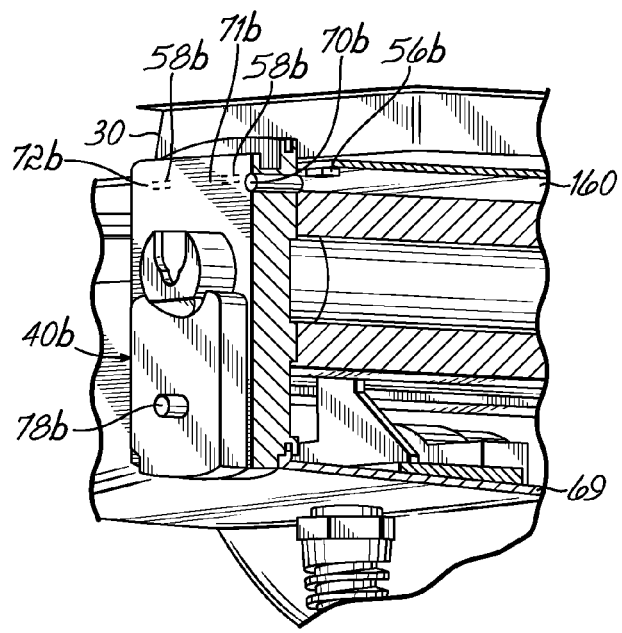
FIG. 7 is a partially disassembled view of the injector powerhead of FIG. 1B illustrating the use of analog Hall-effect sensors in syringe faceplate detection in accordance with the principles of the present invention for detecting faceplates.

FIG. 7 depicts a cut-away view of the portion 40*b* of the powerhead 22 where a faceplate 28*b* mounts, showing the proximity of Hall effect sensors 56*b* and 58*b* to the mounting 40*b*. As noted above, the powerhead has removable faceplates 28*a* and 28*b* (FIG. 1), and different faceplates having differently-sized apertures are used to permit the powerhead 20 to accept differently-sized syringes. For example, one faceplate may be sized for use with low capacity syringes, whereas another is sized for use with larger capacity syringes. Pre-filled syringes may have different sizes or dimensions than syringes which are purchased empty. Different faceplates 28 are needed to accommodate these different syringe sizes. Although the faceplates need not be removed to replace the syringe, they may be removed to use different syringe sizes. It is necessary for the control circuitry on circuit board 160 to be able to detect which faceplate is installed on powerhead 22. Different syringe types may have differing lengths, in which case powerhead 22 must be able to compensate for the length variations when determining the end-of-travel position of the plunger drive ram and when computing the volume of fluid in the syringe. Similarly, syringes of different diameters will produce different flow rates for the same rate of travel of the plunger drive ram; the control circuitry must compensate for this when converting a requested flow rate into movement of the plunger drive ram. Furthermore, pre-fill syringes require a different filling sequence than syringes that are sold empty, and the injector may implement such different sequences when a faceplate used with pre-filled syringes is installed.

For identification purposes, each different faceplate 28 has a unique combination of permanent magnets installed therein, in registration with sensors inside the injector, such as at locations 71*a*/71*b* in the front surface of the drive housing, and/or with a magnetic conductor leading to a sensor, such as at the locations 70*a*/70*b*. Different embodiments of the present invention contemplate different numbers of faceplate magnets and different numbers of corresponding sensors 56 and 58.

To detect the number and positioning of permanent magnets in the faceplate, the circuit board 160 of the powerhead 22 includes associated Hall effect sensors 56*a*/56*b* and 58*a*/58*b* for each magnet that may be present in a faceplate. These sensors 56/58 are positioned near an edge of circuit board 160. Typically, the housing 69 of the powerhead 22 is manufactured of a non-magnetic material such as Aluminum. Accordingly, magnetic fields produced by permanent magnets may penetrate to the Hall effect sensors so that the presence or absence of permanent magnets in a faceplate 28 can be detected remotely from the faceplate 28 by detectors on circuit board 160.

Digital Hall effect sensors have been used in past power injector systems to detect the presence of an injector faceplate. Such a magnetic sensor, however, has a switching threshold that is set at the time of manufacture and is unchangeable. Thus, to detect a magnet, a predetermined minimum amount of flux must be transmitted from the magnet to the sensor. In the manufacturing process of powerhead injectors, there is enough variation from unit to unit that problems exist with digital Hall-effect sensors reliably and accurately detecting the presence or absence of magnets on different faceplates. One solution to this problem is to utilize magnetic conductors which deliver flux to the sensor, as is done at locations 70*a*/70*b*, the use of which as disclosed in U.S. Pat. No. 5,868,710, which is commonly assigned herewith, and is hereby incorporated herein in its entirety. However, magnetic conductors increase manufacturing cost and complexity. Thus, in accordance with the principles of the present invention, the magnetic sensors 56/58 of FIG. 7 are selected to be analog Hall-effect sensors instead of the traditional digital Hall-effect sensors.

Sensors 56*a* and 56*b* detect whether the faceplate is open (by detecting a magnet adjacent to location 70*a*/70*b* on FIG. 1B), and if so, circuit board 160 sends a message to powerpack 26 which prevents any further injection procedures until the faceplate is closed. A magnetic conductor is used at location 70*a*/70*b* due to the likelihood that the magnet carried by movable portions of the faceplate is likely not to be immediately adjacent to the rearwardmost surface of the faceplate 28.

Sensors 58*a* and 58*b*, which are positioned on the circuit board 160 in opposition to locations 71*a*/71*b* and 72*a*/72*b*, detect the size of the faceplate in use. For example, one faceplate, when mounted, may contain a magnet at location 71 and no magnet at location 72, whereas a different faceplate may omit the magnet at location 71 and contain a magnet at location 72. Furthermore, sensors 56*a* and 56*b* may also detect the North-South polarity of a magnet for further discrimination of faceplates, so that a faceplate containing a magnet at location 71 with the North pole facing the injector, can be distinguished from a faceplate containing a magnet at location 71 with the South pole facing the injector. By detecting the North or South orientation of a magnet, as well as the absence of a magnet, three conditions in each of locations 71 and 72 may be identified. This permits eight possible combinations of magnets to identify faceplates (each faceplate must include at least one magnet to permit the injector to identify when no faceplate is mounted). Furthermore, it is within the scope of the present invention to potentially permit the use of opposite polarities in the magnet at location 70*a*/70*b*, so that sensor 58*a*/58*b* not only identifies whether the faceplate is open, but also determines polarity of the magnet at location 70*a*/70*b* to be used in identifying the faceplate. If the North-South polarity detected by sensor 58*a*/58*b* is included in the variables identifying a faceplate, the number of possible combinations of magnets to identify faceplates may be increased to sixteen.

Thus, the circuit board can determine which faceplate has been installed on the A and B side of the injector by determining which of the sensors 58*a* or sensors 58*b* has been triggered, and potentially from the polarity detected by sensor 56*a* or 56*b*. This information is also forwarded to a CPU in the powerpack so that CPU may compensate for the different syringe sizes when controlling the motor 98*a* and 98*b*.

Figure 8:
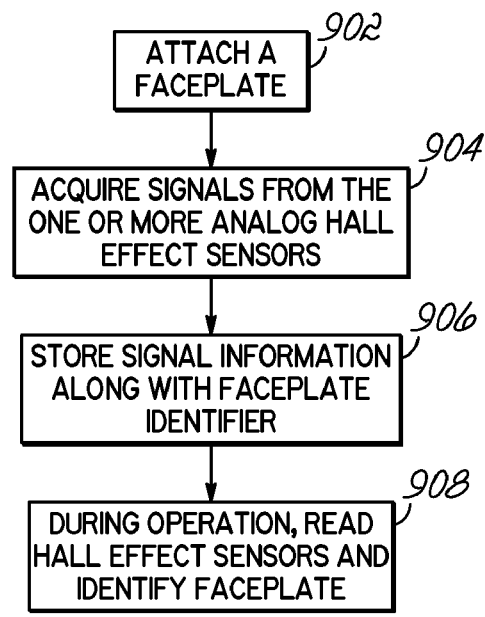
FIG. 8 depicts a flowchart of an exemplary method for detecting different faceplates in accordance with the principles of the present invention.

An advantageous algorithm for utilizing analog Hall-effect sensors in faceplate identification is provided in FIG. 8.

According to this algorithm, a faceplate is attached, in step 902, and then, in step 904, signal levels from the analog Hall-effect sensors are acquired. In one advantageous embodiment, the sensor level readings are acquired with the faceplate attached and another level reading is acquired with the faceplate detached. A threshold value is then determined for each sensor to be approximately halfway between the two level readings. In step 906, this threshold is stored along with a faceplate identifier. Accordingly, during operation of the injector system, the analog Hall-effect sensors can be read by the control circuitry to get a reading that is compared to the stored thresholds. Based on this comparison, the faceplate can more accurately be identified. In other words, the analog Hall-effect sensors, are calibrated for each faceplate and, thus, take into account variations in sensor manufacture, magnet strength, and other variable factors. In certain embodiments, the signals from the sensors are obtained in such a manner that transient signal levels while the faceplate is being positioned on the powerhead are ignored.

As discussed briefly earlier, power injector systems often include automatic protocols that can be selected from a menu screen. An operator will select information about a protocol and then modify certain parameters, if needed, to customize the protocol for each situation. Then, the powerhead can be set in an automatic operating mode that allows the protocol to be performed substantially automatically.

Many power injector systems have a pressure limit feature that serves as a safety feature with respect to proper protocol setup and flow restriction setup. If an operator programmed a flow rate unintentionally too high for a particular fluid path setup, the fluid pressure may increase to an unacceptable level. In other cases, the programmed flow may be properly set but a fluid path blockage may increase the fluid pressure to an unacceptable level. In either instance, the pressure limit feature of the software is activated and takes control of the flow-rate to lower the fluid path pressure to ensure it does not exceed a predetermined amount.

Figure 9:
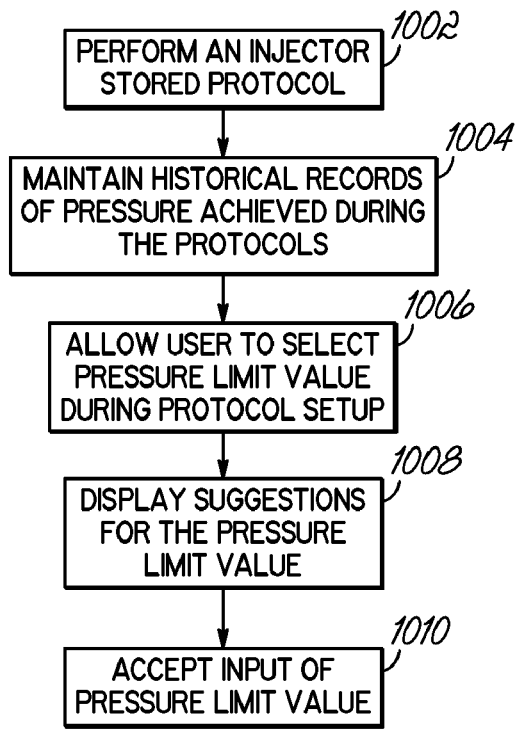
FIG. 9 depicts a flowchart of an exemplary method for suggesting pressure limit values for an injection protocol.

Embodiments of the present invention implement the exemplary algorithm of FIG. 9 to increase the accuracy of the pressure limit setting input by operators. By ensuring that an appropriate pressure limit value is entered by an operator, a number of advantages are provided. Too low of a pressure limit may unnecessarily interrupt a protocol and require the operator to manually perform a number of functions or to manually address various alarms and warnings. If the pressure limit is set too high, the injector may not react to a problem until the pressure increases past an excessively high pressure.

In accordance with the algorithm of FIG. 9, the power injector performs a variety of stored protocols, in step 1002. During the performance of these protocols, historical data is collected and stored, in step 1004, relating to the fluid pressures that were achieved during the protocol. The data that is collected can be statistically analyzed to determine average pressures, highest achieved pressures, statistically significant variations of pressure, standard deviations of achieved pressures, etc.

When an operator retrieves a protocol from memory to perform, the software of the powerhead allows the operator to input a pressure limit value, in step 1006. However, rather than simply relying on the operator's knowledge or experience, the statistical information stored in memory is used to display, in step 1008, a suggestion to the user for what an appropriate fluid limit value would be. The suggested value may be the average fluid pressure, for that protocol, the highest pressure achieved for that protocol, or some fixed percentage above those values. One of ordinary skill will appreciate the many different suggested values can be provided to an operator based on the historical data without departing form the scope of the present invention.

Based on the suggestion, the operator may input a pressure limit value for a protocol, in step 1010. Alternatively, the suggested value may be automatically made a default value that the operator merely confirms as the selected value. Furthermore, regardless of the operator's selected pressure limit, the injector may utilize pressures achieved in previous executions of a protocol to determine thresholds for generating warnings of overpressure, or to abort an injection. For example, one approach of this kind would warn the operator upon detection of a pressure that is greater than a certain number of standard deviations from the mean pressure previously experienced for the current protocol, e.g., more than 1.5 standard deviations above the mean, and abort an injection upon detection of a pressure that is greater than a larger number of standard deviations from the mean pressure previously experienced, e.g., more than 3 standard deviations above the mean.

To facilitate such statistical approaches to pressure limit calculation, the injector would need to build mean and standard deviation figures only from successful, normal executions of a given protocol. Thus, for example, in the event of an overpressure condition detected by the injector, the injector could query the operator whether an abnormal condition such as kinked tubing caused the overpressure condition. If an abnormal condition caused the overpressure condition, then the resulting pressure data would be excluded from future statistical calculations so that the mean and standard deviation data collected by the injector are not skewed by abnormal data.

One useful parameter that impacts many protocols and the method in which they are performed is syringe capacity. In some instances, an operator may be required to input the syringe capacity via an interface screen for pre-filled syringes. The capacity of the syringe may differ even though the outer physical dimensions of the syringe remain the same. The manual entry of this information may sometimes lead to unintentional errors. Accordingly, automatic detection of a pre-filled syringe and its capacity advantageously improves the accuracy and reliability of automatic protocols in powered injector systems.

Figure 10:
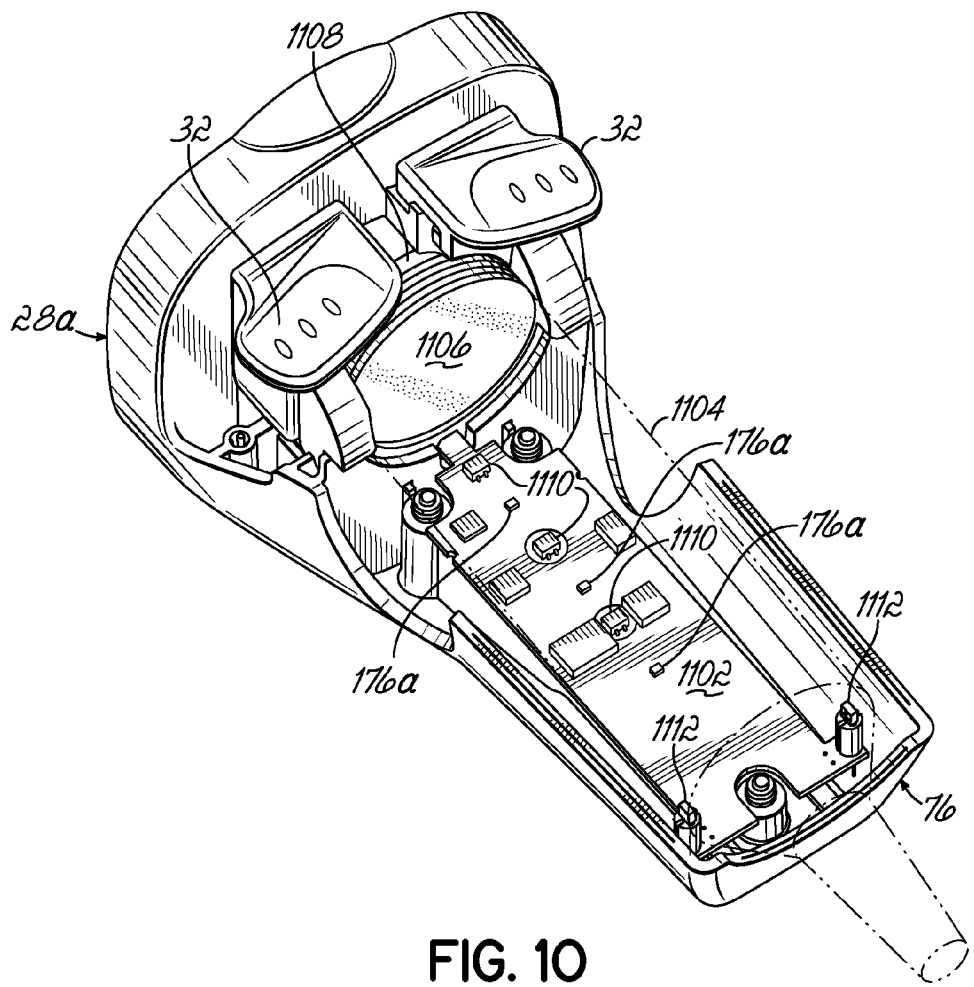
FIG. 10 is a partially disassembled view of a faceplate for the injector powerhead of FIG. 1B illustrating the electrical components therein including the sensor arrangement to detect attributes of a syringe in accordance with principles of the present invention.

FIG. 10 illustrates the circuit board 1102 containing faceplate electronics of a 125 ml faceplate as discussed above. This circuit board utilizes sensors in an exemplary detection system, the operation of which is detailed in FIGS. 11A-C. In these figures, the control board 1102 houses a series of sensors 1110 and 1112. As shown and discussed with reference to FIG. 2, this board 1102 is in communication with the main circuit board 160 (FIG. 2) that controls the operation of the powerhead. Through this communications channel, information detected by the sensors 1110 and 1112 may be transmitted to the main board 160 for additional analysis or as information to use when controlling a protocol performance.

Circuit board 1102 may be housed within a housing or other support structure that at least partially surrounds the circuit board 1102 and the syringe 1104. One such housing is housing 76 shown on the powerhead of FIG. 1B. The housing 76 includes a cradle area 1120 (FIG. 11C) that provides the physical support of the syringe 1104 while attached to a powerhead assembly, and hold the circuit board 1102 in a fixed position relative to the syringe 1104.

Sensors 1110 emit radiation of a particular wavelength and detect reflection of that radiation. In particular, infrared radiation levels are effective because the syringe 1104 is substantially transparent at that wavelength while the plunger 1106 is non-reflective. The plunger backer disc 1108, however, is reflective and therefore is detected by one of the sensors 1110. The plunger backer disc 1108 is located differently in FIG. 11A as compared to FIG. 11B. Thus, a different detector 1110 will detect the presence of the disc 1108 in each instance. For example, the rightmost sensor 1110 detects the disc 1108 for the 125 mL syringe of FIG. 11A while the left-most sensor 1110 detects the disc 1108 for the 50 mL syringe of FIG. 11B. The exemplary sensor board 1102 of these figures include three sensors 1110 because conventionally sized syringes typically encompass the range of locations of these three sensors. However, one of ordinary skill would recognize that fewer or more sensors 1110 could be used without departing from the scope of the present invention.

Figure 11C:
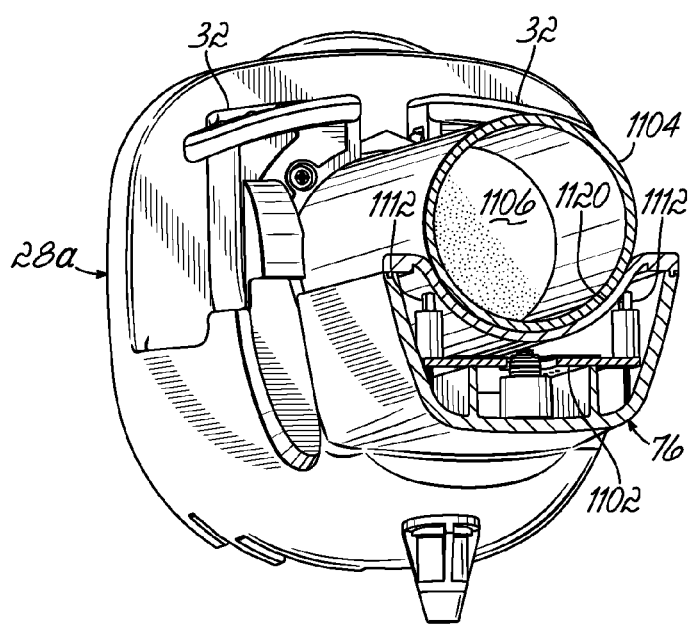
FIGS. 11A-11C illustrate different views of a sensor arrangement to detect attributes of a syringe in accordance with the principles of the present invention.
Figure 11A:
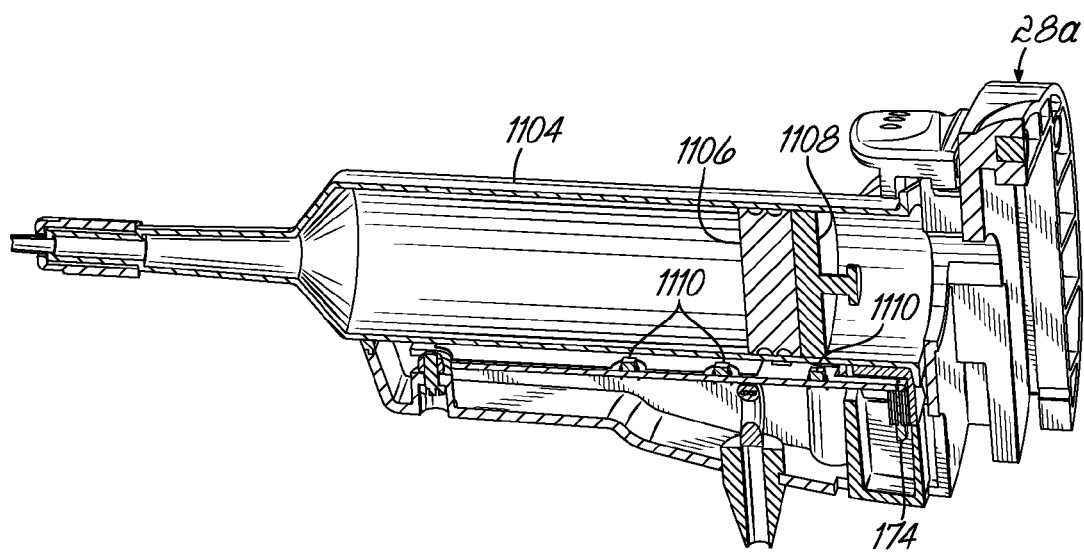
Figure 11B:
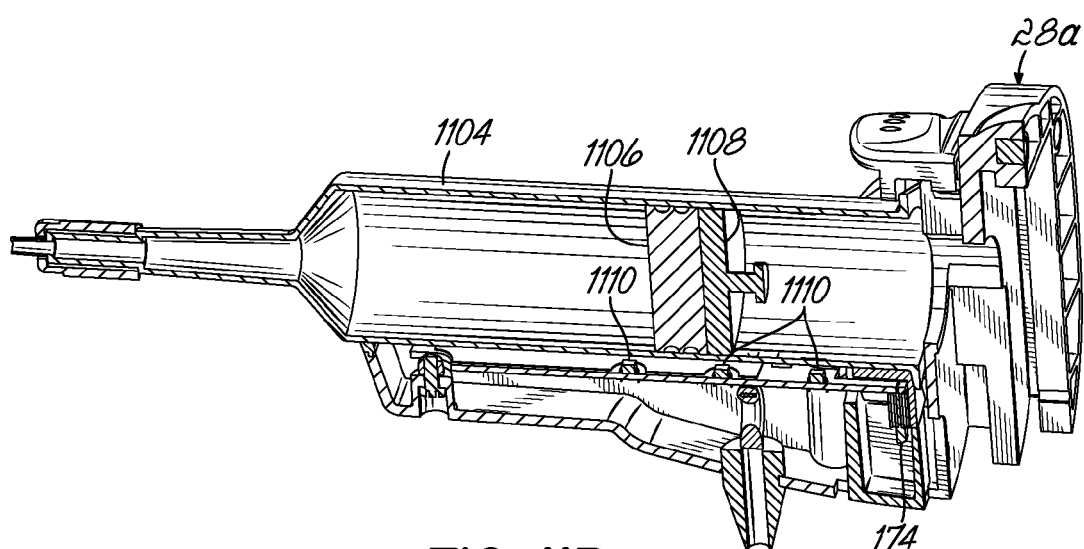

A pair of sensors 1112 is also depicted in FIGS. 11A-C. In this pair of sensors, one acts as a transmitter and the other as a receiver. If the optical path between the two sensors 1112 is blocked then a different signal results than if it is open. For example, presence of fluid within the syringe 1104 will attenuate the signal between the two sensors 1112 as compared to when the syringe 1104 is empty. Accordingly, the sensors 1112 can be used to detect when the syringe is empty.

Ambient light may impinge on the sensors 1110 and impact the accuracy of their readings. Accordingly, one embodiment of the present invention contemplates sensors 1110 that time modulate their output so that reception of unmodulated return signals can be discarded as unwanted noise. In addition, or alternatively, the cradle 1120 may be constructed of material that reflects ambient light and, therefore, protects the sensors 1110 from excessive ambient light. In addition, conventional syringe and power injector features such as syringe heaters may be included such that they do not interfere with operation of the sensors 1110 and 1112.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A contrast media injector system comprising:
   a faceplate mounting region at which magnetic sources of a faceplate may be located;
   a Hall effect sensor associated with a location of said faceplate mounting region at which a magnetic source of a faceplate may be located;
   an analog circuit configured for measuring an analog signal representative of magnetic flux impinging upon said Hall effect sensor;
   a stored threshold analog signal value that is of an analog magnitude that is between first and second signal levels, said first signal level being from a first analog signal output by said Hall effect sensor when a faceplate is attached to said faceplate mounting region, and said second signal level being from a second analog signal output by said Hall effect sensor when the same faceplate is detached from said faceplate mounting region; and
   a control circuit coupled to said analog circuit for determining whether a magnetic source of a faceplate has one of at least three states based upon said analog signal and said stored threshold analog signal value.

2. The system of claim 1, wherein said faceplate mounting region is configured to attach to a faceplate having one or more magnets each associated with a respective magnetic conductor such that a presence, absence, and/or polarity of at least one of said one or more magnets on the faceplate is detected by a respective Hall effect sensor.

3. The system of claim 1, further comprising:
   a memory configured to store, for each of a plurality of faceplates, a respective state representing an analog signal representative of magnetic flux impinging on said Hall effect sensor.

4. Within a contrast media injector system, a method comprising:
   attaching a faceplate to a powerhead of a contrast media injector system, wherein said faceplate comprises one or more magnets;
   acquiring with a Hall effect sensor a first analog signal representative of magnetic flux impinging on said Hall effect sensor with said faceplate attached;
   acquiring with said Hall effect sensor a second analog signal representative of magnetic flux impinging on said analog Hall effect sensor with said faceplate detached; and
   storing a signature for said faceplate based on each of said first and second analog signals, wherein said signature comprises a stored threshold analog signal value that is between first and second signal levels from said first and second analog signals, respectively.

5. The method of claim 4, wherein said stored threshold analog signal value is approximately halfway between said first and second signal levels from said first and second analog signals, respectively.

6. The method of claim 4, further comprising:
   storing a respective signature for each of a plurality of faceplates.

7. The method of claim 6, further comprising:
   attaching an unknown faceplate to said powerhead;
   determining a detected analog signal level and/or polarity for said Hall effect sensor; and
   identifying said unknown faceplate based on said detected signal levels and said stored signatures.

8. The system of claim 1, wherein said control circuit utilizes said stored threshold value to determine whether a faceplate attached to said faceplate mounting region includes a corresponding magnetic source.

9. The system of claim 1, further comprising:
   a plurality of said Hall effect sensors; and
   a memory comprising a plurality of faceplate identifiers, wherein each of said plurality of faceplate identifiers is associated with a unique combination of states derived from said analog signal from each of said plurality of Hall effect sensors.

10. A contrast media injector system comprising:
    a faceplate mounting region at which one or more magnetic sources of a faceplate may be located;
    a plurality of Hall effect sensors each associated with a location of said faceplate mounting region at which a magnetic source of a faceplate may be located;
    an analog circuit configured for measuring an analog signal representative of magnetic flux impinging upon said each said Hall effect sensor;
    a stored threshold analog signal value associated with each said Hall effect sensor, wherein each said stored threshold analog signal value is of a magnitude that is between first and second signal levels, said first signal level being from a first analog signal output by the corresponding said Hall effect sensor when a faceplate is attached to said faceplate mounting region, said second signal level being from a second analog signal output by the corresponding said Hall effect sensor when the same faceplate is detached from said faceplate mounting region;

a control circuit coupled to said analog circuit for determining a state from said analog signal from each said Hall effect sensor and utilizing the corresponding said threshold analog signal value; and a stored faceplate identifier that is associated with a first combination of said states.

* * * * *